(12) United States Patent
Childers et al.

(10) Patent No.: US 7,390,387 B2
(45) Date of Patent: Jun. 24, 2008

(54) METHOD OF SORTING CELLS IN SERIES

(75) Inventors: Winthrop D. Childers, San Diego, CA (US); David Tyvoll, La Jolla, CA (US); Kirk Norton, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 881 days.

(21) Appl. No.: 10/808,803

(22) Filed: Mar. 25, 2004

(65) Prior Publication Data

US 2005/0211557 A1   Sep. 29, 2005

(51) Int. Cl.
*G01N 27/447* (2006.01)
*G01N 27/453* (2006.01)

(52) U.S. Cl. ........................... 204/547; 204/643
(58) Field of Classification Search .......... 204/547, 204/643
See application file for complete search history.

(56) References Cited

U.S. PATENT DOCUMENTS

| | | | |
|---|---|---|---|
| 4,874,507 A | 10/1989 | Whitlock |
| 4,911,806 A | 3/1990 | Hofmann |
| 5,126,022 A | 6/1992 | Soane et al. |
| 5,344,535 A | 9/1994 | Betts et al. |
| 5,454,472 A | 10/1995 | Benecke et al. |
| 5,589,047 A | 12/1996 | Coster et al. |
| 5,626,734 A | 5/1997 | Docoslis et al. |
| 5,653,859 A | 8/1997 | Parton et al. |
| 5,814,200 A | 9/1998 | Pethig et al. |
| 5,858,192 A | 1/1999 | Becker et al. |
| 5,938,904 A | 8/1999 | Bader et al. |
| 5,993,630 A | 11/1999 | Becker et al. |
| 5,993,631 A | 11/1999 | Parton et al. |
| 6,056,861 A | 5/2000 | Fuhr et al. |
| 6,059,950 A | 5/2000 | Dames et al. |
| 6,149,789 A | 11/2000 | Benecke et al. |
| 6,193,866 B1 | 2/2001 | Bader et al. |
| 6,197,176 B1 | 3/2001 | Pethig et al. |

(Continued)

FOREIGN PATENT DOCUMENTS

WO          WO 97/34689          9/1997

(Continued)

OTHER PUBLICATIONS

Tsuda, Takao, Yamauchi, Norihiro, and Kitagawa, Shinya, "Separation of Red Blood Cells at the Single Cell Level by Capillary Zone Electrophoresis", Analytical Sciences, vol. 16, pp. 847-850 (Aug. 2000).

(Continued)

*Primary Examiner*—Alex Noguerola (57) ABSTRACT

A method of sorting cells comprises providing a fluid flow path for cell movement through a series of cell sorters in a first direction with an output of a preceding cell sorter of the series communicating with an input of a successive cell sorter of the series. Within each cell sorter, a first portion of the cells is separated from a second portion of the cells by applying a first non-uniform electric field via a first electrode array to cause movement of the first portion of the cells in a second direction across the fluid flow path, having a component generally transverse to the first direction into the output of a respective cell sorter.

19 Claims, 5 Drawing Sheets

U.S. PATENT DOCUMENTS

| | | | |
|---|---|---|---|
| 6,264,815 B1 | 7/2001 | Pethig et al. | |
| 6,287,832 B1 | 9/2001 | Becker et al. | |
| 6,306,272 B1 | 10/2001 | Soane et al. | |
| 6,310,309 B1 | 10/2001 | Ager et al. | |
| 6,403,367 B1 | 6/2002 | Cheng et al. | |
| 6,465,225 B1 | 10/2002 | Fuhr et al. | |
| 6,537,433 B1 | 3/2003 | Bryning et al. | |
| 6,540,895 B1 | 4/2003 | Spence et al. | |
| 6,596,143 B1 | 7/2003 | Wang et al. | |
| 6,610,188 B1 | 8/2003 | Fuhr et al. | |
| 6,641,708 B1 | 11/2003 | Becker et al. | |
| 6,660,493 B2 | 12/2003 | Miles | |
| 6,673,225 B1 | 1/2004 | Arnold | |
| 6,685,812 B2 | 2/2004 | Miles | |
| 6,727,451 B1 | 4/2004 | Fuhr et al. | |
| 6,730,204 B2 | 5/2004 | Mariella, Jr. | |
| 6,749,736 B1 | 6/2004 | Fuhr et al. | |
| 6,761,811 B2 | 7/2004 | Mariella, Jr. | |
| 6,964,736 B2 * | 11/2005 | Quake et al. | 204/452 |
| 7,169,282 B2 * | 1/2007 | Talary et al. | 204/670 |
| 2002/0005354 A1 | 1/2002 | Spence et al. | |
| 2002/0036141 A1 | 3/2002 | Gascoyne et al. | |
| 2002/0042125 A1 | 4/2002 | Peterson et al. | |
| 2002/0055167 A1 | 5/2002 | Pourahmadi et al. | |
| 2002/0076825 A1 | 6/2002 | Cheng et al. | |
| 2002/0182627 A1 | 12/2002 | Wang et al. | |
| 2002/0182654 A1 | 12/2002 | Jing et al. | |
| 2003/0010637 A1 | 1/2003 | Cummings | |
| 2003/0121788 A1 | 7/2003 | Gascoyne et al. | |
| 2003/0134416 A1 | 7/2003 | Yamanishi et al. | |
| 2003/0159932 A1 | 8/2003 | Betts et al. | |
| 2004/0011652 A1 | 1/2004 | Bressler | |

FOREIGN PATENT DOCUMENTS

| | | |
|---|---|---|
| WO | WO 98/10869 | 3/1998 |
| WO | WO 02/12896 | 2/2002 |
| WO | WO 02/28523 | 4/2002 |
| WO | WO 03/014291 | 2/2003 |
| WO | WO 03/093496 | 11/2003 |

OTHER PUBLICATIONS

Holmes, David and Morgan, Hywet, "Cell Positioning and Sorting Using Dielectrophoresis", European Cells and Materials, vol. 4, Suppl. 2, pp. 120-122, (2000).

Swiss Center for Electronics and Microtechnology, "Dielectrophoretic Size-Sensitive Particle Filter for Micro-Fluidic Applications", 2 pgs., printed Feb. 24, 2004 from www.csem.ch/corporate/Report2002/pdf/microrobotics.pdf.

* cited by examiner

METHOD OF SORTING CELLS IN SERIES

CROSS-REFERENCE TO RELATED APPLICATIONS

This application is related to U.S. patent application Ser. No. 10/808,945, entitled "METHOD OF SORTING CELLS ON A BIODEVICE", and U.S. patent application Ser. No. 10/808,897, now U.S. Pat. No. 7,160,425 entitled "CELL TRANSPORTER FOR A BIODEVICE", both filed on Mar. 25, 2004, and incorporated herein by reference.

BACKGROUND

The rapid miniaturization in electronic devices, particularly their manufacture and assembly, has transformed the medical industry. In particular, handling and testing of cells and other components within body fluids has moved beyond the conventional test tube to other devices, such as biochips. A biochip, sometimes called a lab-on-a-chip, refers to the placement of biologic materials on a miniature electronic device that is capable of electrically and/or chemically interacting with the biologic materials for testing or other purposes.

Considerable efforts have been made in the biochip environment to apply electric fields to manipulate cells, including their movement, separation, property determination, etc. Despite numerous attempts at cell manipulation with electric fields, the ability to manipulate cells is still limited by different characteristics of the cells, such as cell size, cell aggregation, cell polarizability, etc. For example, enriching one type of cells from other types of cells is challenged by the great variety of sizes, shapes, polarizability, and relative volumes of cells within a fluid. Impeding the enrichment of certain types of cells on the biochip, in turn, hampers the ability to perform other functions on those cells, such as testing, harvesting, and processing for further analyses.

For these reasons, among others, widespread use of biochip devices has been limited.

DETAILED DESCRIPTION

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Embodiments of the present invention are directed to a sorter assembly of a biodevice configured for sorting a population of different types of cells into a target group of cells and a non-target group of cells. In referring to a "type" of cell versus another "type" of cell, the term "type" refers to any distinguishing characteristic (such as size, shape, and/or whether the cell is nucleated) that may affect an electrical characteristic of the cell that enables sorting by embodiments of the present invention.

In one embodiment, the biodevice comprises a plurality of cell sorters arranged in series. Each cell sorter moves the cells along a fluid flow path in a first direction to separate a first portion of cells (e.g., target cells) from a second portion of cells (e.g., non-target cells). An output of a preceding cell sorter directs the first portion of cells into an input of a subsequent cell sorter in the series. With this arrangement, the sorter assembly of the biodevice progressively enriches the first portion of cells (e.g., target cells).

To perform this sorting operation, each cell sorter comprises one or more electrode arrays configured to apply an electric field that induces cells that respond to the electric field (i.e., field-responsive cells) to move with a velocity component in a second direction generally transverse to the first direction for flow into a first output of the cell sorter. Cells that do not respond (or respond substantially less) to the electric field (i.e., non-responsive cells) are permitted to flow along the fluid flow path in the first direction into a second output of the cell sorter. Cells that move into the first output are directed to the input of a subsequent cell sorter while cells that move into the second output are not directed to a subsequent cell sorter. Cells that move into the second output are collected into a common pathway with cells exiting other cells sorters, or are discarded as waste.

A frequency of the applied electric field, as well as the electrical characteristics of each cell and the surrounding medium, determine which portions of cells respond to the electric field and which portions of cells do not respond to the electric field (or respond substantially less to the field). Accordingly, one can select which cells are the target cells or non-target cells by selecting a frequency at which the particular type of cells either respond or do not respond to the field (or respond substantially less to the field), respectively.

In one embodiment, field-responsive cells that move into the first output are the target cells and the non-responsive cells that move into the second output are the non-target cells. In other embodiments, non-responsive cells that move into the second output are the target cells while the field-responsive cells that move into the first output are the non-target cells.

In one embodiment, each cell sorter in series operates at substantially the same frequency so that repeated sorting occurs at a single frequency. In other embodiments, at least two cell sorters in the series operate at different frequencies. In this embodiment, sorting is performed successively at different frequencies with each frequency being selected to separate out a different type of cell into the first output or into the second output. In this way, the series of cell sorters systematically removes a different type of cell at each cell sorter. The cells can be of a different type based on size, shape or other distinguishing characteristic of the cells. This process is repeated through successive cell sorters in the series as many times as necessary, with as many different frequencies as necessary, to discard many different types of cells, one type at a time, until substantially only the target cells are left for collection. In one embodiment, the target group of cells comprises only one type of cells while in other embodiments, the target group of cells comprises more than one type of cells.

In one embodiment, each cell sorter within the series employs the same type of electrode arrangement for applying the electric field that acts as a separating influence. In other embodiments, some of the cell sorters within the series include different types of electrode arrangements for applying the first electric field to influence cell separation. Each of these different types of electrode arrangements are described below in association with FIGS. 4-8.

In one embodiment, cells are moved along the fluid flow path in the first direction by fluid pressure. In other embodiments, cells are moved along the fluid flow path by an electrode array that applies a non-uniform electric field that is temporally varying to induce cell transport along the fluid flow path in the first direction.

In some embodiments, multiple sorter assemblies, each comprising a series arrangement of cell sorters, are arranged in parallel on one or more chips to enable sorting larger volumes of cells.

In some embodiments, a dielectrophoretic field can be applied by the biodevice to impart a separating influence on cells flowing through the cell sorter and/or to impart a transport movement of the cells to travel through the fluid flow path. This dielectrophoretic field can be defined as an electric field that varies spatially or is non-uniform where it is being applied to the particles (e.g., cells). Positive dielectrophoresis occurs when the particle (e.g., cell) is more polarizable than the medium (e.g., buffer) and results in the particle being drawn toward a region of higher field strength. A system operating in this way can be referred to as operating in a positive dielectrophoresis mode. Negative dielectrophoresis occurs when the particle is less polarizable than the medium and results in the particle being drawn toward a region of lesser field strength. A system operating in this way can be referred to as operating in a negative dielectrophoresis mode. First, these electric fields are generated by applying a voltage between two or more electrodes. The field electrodes are disposed and arranged in a geometric relationship relative to one another to cause a non-uniformity or spatial variation in the applied electric field, which produces the dielectrophoretic effect. Accordingly, selectively applied variations in this geometric relationship of the field electrodes are used to cause desired movements of cells within the dielectrophoretic fields.

Second, by applying a time varying voltage to the field electrodes, a temporally varying electric field can be produced. This time variation will tend to affect the polarization of the fluid medium and the particles differently—hence it will affect the relative polarization between the fluid medium and the particles. Accordingly, selective application of time variance in the dielectophoretic field can be used to move cell particles in a desired manner.

In many cases, particularly where the variation is sinusoidal, the time variation has a characteristic frequency. The relative polarization of a particle relative to the medium is typically affected by the applied frequency. Large changes in frequency can be sufficient to change a system from operating in a negative dielectrophoresis mode to a positive dielectrophoresis mode. For example, there may be one frequency wherein the cells move toward regions of higher field strength (the positive dielectrophoresis mode) and another frequency wherein the cells move away from regions of higher field strength (the negative dielectrophoresis mode). Either negative or positive dielectrophoresis may be used in the embodiments of the present invention to move cells within a fluid medium.

Third, when using more than two field electrodes, certain types of motion can be induced by selectively shifting which pair of electrodes has a voltage difference or using an amplitude modulation technique. For example, an arrangement of four interleaved and independent field electrodes can induce a "traveling wave dielectrophoresis" response in the particles to allow controlled translation of the particles. This "traveling wave" effect is used to impart a separating influence on cells by causing field-responsive cells to move with a velocity component in a second direction, generally transverse to a flow of cells in a first direction, through the cell sorter and/or to impart a transportational influence on cells to flow in the first direction through the cell sorters of the biodevice.

Figure 1:
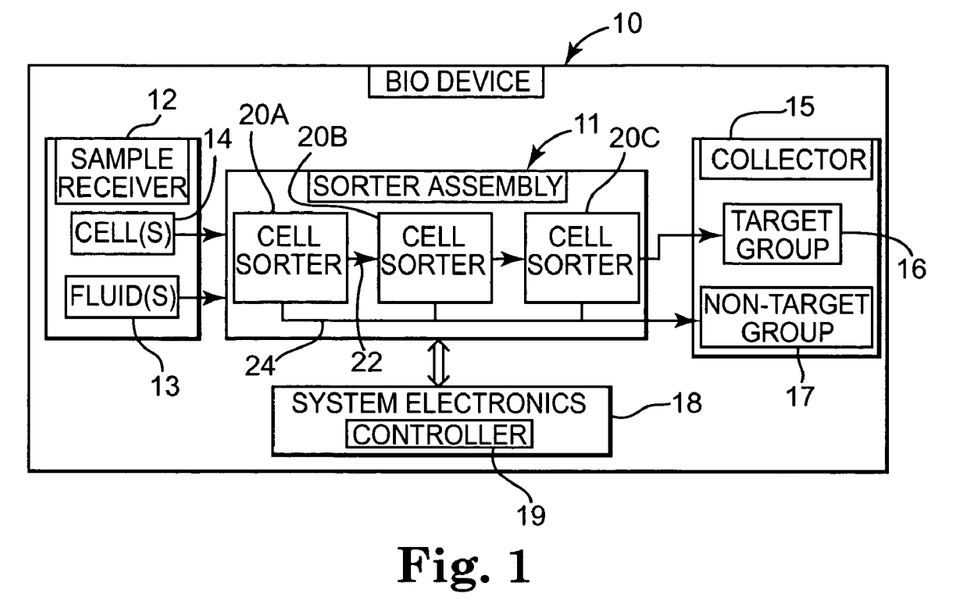
FIG. 1 is a block diagram of a cell sorter system, according to an embodiment of the present invention.

In one embodiment shown in FIG. 1, biodevice 10 is directed to receive a sample of cells within a fluid, sort the cells into different groups, and then collect the cells. As shown in FIG. 1, biodevice 10 comprises sample receiver 12, sorter assembly 11, and cell collector 15. Sample receiver 12 includes fluid source(s) 13 and cell source(s) 14 while cell collector 15 comprises target group 16 of cells and non-target group 17 of cells. Biodevice 10 also comprises system electronics 18 with controller 19.

Fluid source(s) 13 provide one or more types of fluid and/or fluid mediums for use on biodevice 10 while cell source(s) 14 provide one or more types of cells suitable for handling and testing on biodevice 10. Fluid source(s) 13 of biodevice 10 include, but are not limited to, one or more sources of fluid mediums, such as fluid suspensions, reagent solutions, blood and blood derivatives, etc. Cell source(s) 14 comprise a population of cells including different type of cells from one or more sources and that are capable of being sorted into at least a group of target cells and a group of non-target cells. In some embodiments, the target cells include one type of cells while in other embodiments, the target cells include more than one type of cells. Likewise, in some embodiments, the non-target cells include one type of cells while in other embodiments, the non-target cells include more than one type of cells. Cell sources(s) 14 within biodevice 10 include, but are not limited to, one or more sources of cells, such as human cells, animal cells, etc, as well as other particles, such as cell organelles, analytes, bacteria, viruses, etc, including combinations of the same.

System control electronics 18 of biodevice 10 is in electrical communication with sample receiver 12, sorter assembly 11, and cell collector 15. System control electronics 18 directs various functions of biodevice 10 including operation of controller 19 which is configured to direct various electric fields. In one embodiment, as further described in association with FIG. 2, controller 19 comprises a signal generator that enables waveforms (temporally varying and non-temporally varying) that are operable at selectable magnitudes (e.g., voltages), frequencies, phases, and polarities (e.g., negative or positive frequencies). In some embodiments, this signal generator is capable of generating signal frequencies in the range from DC to several GHz.

As also shown in the embodiment of FIG. 1, sorter assembly 11 of biodevice 10 comprises cell sorter 20A, cell sorter 20B, and cell sorter 20C arranged in series. Each cell sorter 20A, 20B, 20C separates one type of cells, e.g., target cells, from another type of cells, e.g., non-target cells. In addition, an enrichment pathway 22 directs an output of target cells from a preceding cell sorter 20A, 20B into the input, respectively, of a subsequent cell sorter 20B, 20C. Meanwhile, a secondary pathway 24 of non-target cells from any one of cells sorters 20A-20C directs the non-target cells for collection for other purposes or for discard.

With this arrangement, a first portion of cells (e.g., target cells) becomes progressively enriched to include a greater concentration of the first portion of cells (e.g., target cells) and a lower concentration of a second portion of cells (e.g., non-target cells). Meanwhile, the second portion of cells (e.g., non-target cells) also become more concentrated with a greater concentration of the second portion of cells (e.g., non-target cells) and a lower concentration of the first portion of cells (e.g., target cells). In one embodiment, when this progressive enrichment mechanism is operated at optimal effectiveness, the first portion of cells (e.g., non-target cells) will contain few, if any of the second portion of cells (e.g., non-target cells). After passage through all of the cell sorters 20A, 20B, 20C of sorter assembly 11, the cells are collected within cell collector into target group 16 of cells and non-target group 17 of cells.

As described in association with FIGS. 4-8, various electrode arrangements are employed within each cell sorter 20A, 20B, 20C for applying an electric field to separate the target cells from the non-target cells. In one embodiment, each cell sorter 20A, 20B, 20C within the series can be configured with substantially the same type of electrode arrangement for separating cells while in other embodiments, at least two of the cell sorters 20A, 20B, 20C within the series are configured with different types of electrode arrangements for separating cells.

Figure 2:
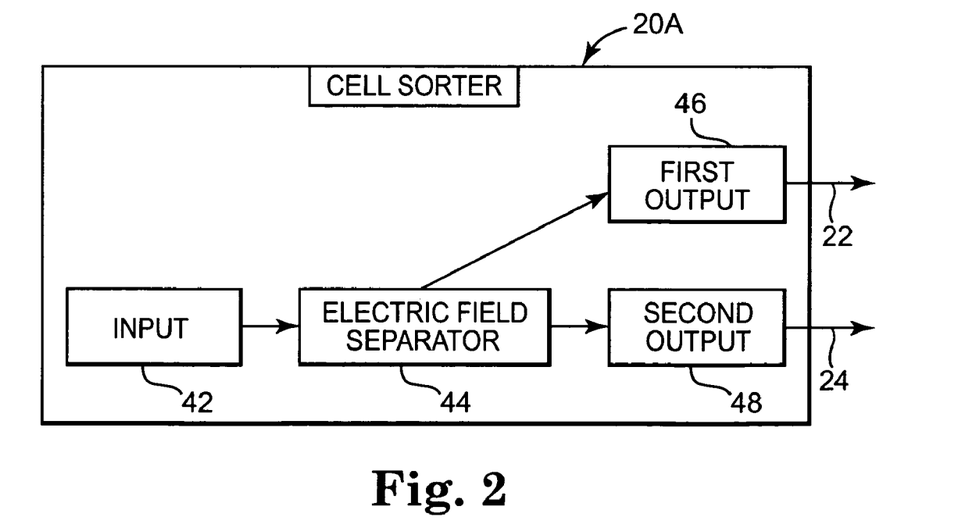
FIG. 2 is a block diagram of a cell sorter, according to an embodiment of the present invention.

As shown in the embodiment of FIG. 2, cell sorter 20A, which corresponds to any one of cell sorters 20A, 20B, 20C, comprises cell input 42, electric field separator 44, first output 46 (e.g., a first port) and second output 48 (e.g., a second port). Cell input 42 receives cells within a fluid medium from sample receiver 12, and then the cells are electrically separated, via application of one or more electric fields to the cells, into a first portion of cells and a second portion of cells. The first portion of cells, which are responsive to electric field separator 44, move into the first output 46 while the second portion of cells, which are not influenced (or influenced substantially less) by electric field separator 44, are permitted to flow into the second output 48. First output 46 directs cells for entry into a subsequent cell sorter via enrichment pathway 22 while second output 48 directs cells away from cell sorter 20A via secondary pathway 24 for discard or for other purposes.

Figure 3:
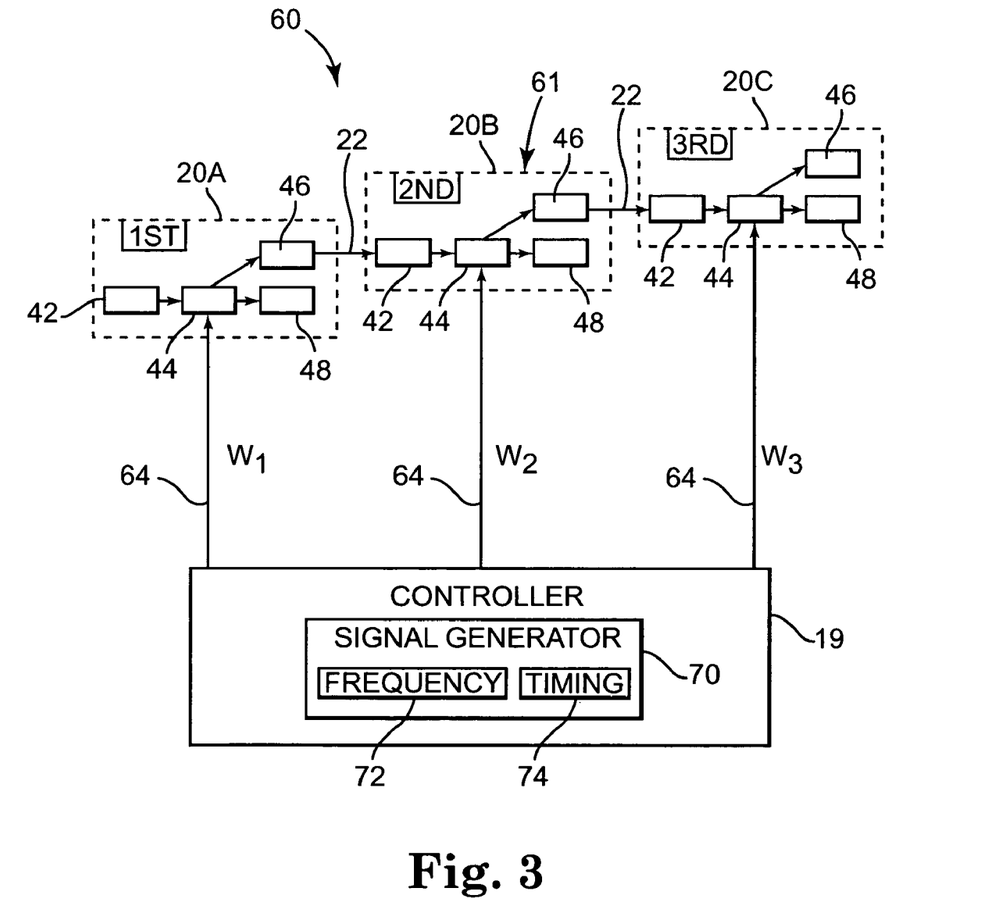
FIG. 3 is block diagram of a cell sorter system, according to another embodiment of the present invention.

In one embodiment, as shown in FIG. 3, system 60 comprises an array 61 of cell sorters 20A, 20B, 20C, controller 19 with signal generator 70. Cell sorter array 61 includes first cell sorter 20A, second cell sorter 20B, and third cell sorter 20C. In one embodiment, each cell sorter 20A, 20B, 20C comprises features and attributes substantially the same as described for cell sorter 20A of FIGS. 1-2, such as cell input 42, electric field separator 44, first output 46 and second output 48. The contents of first output 46 from cell sorter 20A are fed via enrichment pathway 22 into cell input 42 of subsequent cell sorter 20B. Likewise, the contents of first output 46 from cell sorter 20B are fed, via enrichment pathway 22, into cell input 42 of subsequent cell sorter 20C. In this way, the group of target cells is progressively enriched through each stage in the series of cell sorters.

As further shown in the embodiment of FIG. 3, electric field separator 44 of each cell sorter 20A, 20B, 20C is in electrical communication with controller 19 of system control electronics 18 via link 64. Electric field separator 44 of each cell sorter 20A, 20B, 20C includes an electrode arrangement (shown in FIGS. 4-5, and 8) that is driven by electrical signals from signal generator 70 at a frequency, $\omega_1$, $\omega_2$, $\omega_3$, for each cell sorter 20A, 20B, 20C, respectively.

As further shown in the embodiment of FIG. 3, controller 19 of system control electronics 18 (FIG. 1) comprises signal generator 70 having frequency module 72 and timing module 74. Frequency module 72 of signal generator 70 is configured to generate a waveform at one or more frequencies suited for inducing a separating influence between cells that respond to an electric field with movement (i.e., field-responsive cells) and cells that do not respond (or respond substantially less) to the same electric field with movement (i.e., non-responsive or weakly responsive cells). Controller 19 also comprises timing module 74, which enables selective activation and deactivation of electric fields in electric field separator(s) 44 of cell sorter(s) 20A, 20B, 20C.

In some embodiments (in association with the embodiments of FIGS. 4 and 8), timing module 74 activates electrode elements within an electrode array of electrode elements configured to impart a traveling wave within the non-uniform electric fields. In other embodiments (in association with the embodiment of FIG. 5), timing module 74 activates individual elements of an electrode array one at a time (or two at a time) in sequence for a discrete period of time to cause cells to move a limited distance within a fluid medium under the influence of the non-uniform electric field. These limited cell movements are repeated by successive elements of the electrode array to cause a progressive movement of the responsive cells in the second direction across the fluid flow path toward the first output 46 and into enrichment pathway 22.

Different types of cells (based on size, shape, and/or other distinguishing characteristics) and different fluid media have different polarization properties and hence different responses to a given frequency of a non-uniform electric field. Generally, given a particular surrounding media, the electric field will exert a different net force on one type of cell versus another cell type. For some cell/media combinations there is a crossover frequency between negative and positive dielectrophoresis wherein the field exerts no net force on the cell.

But in general, given a cell mixture of two or more cell types, a fluid media and operating frequency are selected that provide a relatively strong net force on a first portion of the cell mixture and a relatively small (or preferably essentially a zero) net force on a second portion of the cell mixture. In one embodiment, the first portion of the cell mixture includes target cells and the second portion of the mixture includes non-target cells. In other embodiments, the first portion of cells are non-target cells, and the second portion of cells are target cells.

In one embodiment, selecting target cells is performed in a negative dielectrophoretic mode to move the cell to lower field regions, thereby enhancing the viability of the cell. Moreover, in some embodiments, at least two cell sorters within the series are operated at different separating frequencies, so that each cell sorter exerts a separating influence on a different type of cells. In this way, each cell sorter in the series successively separates out a different type or class of cells.

While three cell sorters 20A, 20B, 20C are shown in FIGS. 1 and 3, in some embodiments, more than three cell sorters can be used and in other embodiments, less than three cell sorters (e.g., two cell sorters) can be used. For example, in one embodiment, to apply five different separating frequencies for separating five different type of cells, five cell sorters are arranged in series to perform five successive sorting operations.

For example, in an embodiment of two cell sorters in series, a first sorter (e.g., cell sorter 20A) is operated at a first frequency and a second sorter (e.g., cell sorter 20B) is operated at a second frequency. In this embodiment, a first portion of cells and a third portion of cells are field-responsive to the first frequency while the second portion responds substantially less (or not at all) to the first frequency. In addition, only the first portion of cells is field-responsive to the second frequency. Accordingly, when the first and second cell sorters are arranged in series, the first portion of cells and the third portion of cells are separated from a second portion of cells within the first sorter by the electric field applied at the first frequency. The first portion of cells and the third portion of cells are directed from an output of the first sorter into the second sorter. Upon application of the electric field at the second frequency within the second sorter, the first portion of cells are separated from the third portion of cells and directed into an output for collection as target cells.

Figure 4:
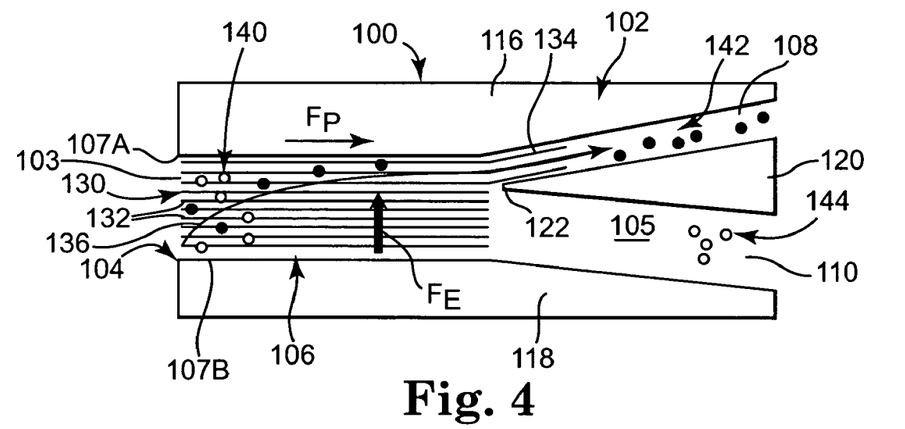
FIG. 4 is a plan view schematically illustrating a cell sorter, according to another embodiment of the present invention.

FIG. 4 illustrates sorter 100, which is one embodiment of cell sorters 20A-C (FIGS. 1-3). As shown in FIG. 4, sorter 100 comprises body 102 that defines a fluid flow path 104. Fluid flow path 104 comprises entrance 103, main path 106, first path 108 and second path 110 with fluid 105 disposed within paths 106, 108, 110. Body 102 comprises first body portion 116, second body portion 118 and flow diverter 120 with apex 122, all of which together define fluid flow path 104. First path 108 corresponds generally to first output 46 of cell sorter 20A-20C (FIG. 2) and second path 108 corresponds generally to second output 48 of cell sorters 20A-20C (FIG. 2).

As further shown in the embodiment of FIG. 4, sorter 100 comprises electrode array 130, which is an embodiment of electric field separator 44 of cell sorter 20 (FIG. 2). Electrode array 130 comprises a plurality of electrode elements 132 arranged generally parallel to each other, and generally parallel to a longitudinal axis of path 106. A portion 134 of electrode array 130 extends into first path 108.

In use, as shown in FIG. 4, a population of cells 140 of different types of cells travel down fluid flow path 104 under fluid pressure in a first direction (represented by directional force arrow $F_P$). As these cells 140 travel through main path 106, electrode array 130 applies a temporally varying non-uniform electric field (represented by directional force arrow $F_E$) that induces field-responsive cells 142 to move with a velocity component in a second direction away from second side 107B of main path 106 toward first side 107A of main path 106 so that a greater number of field-responsive cells 142 move into first path 108 than second path 110. In one embodiment, a typical or average path of field-responsive cells moving under the influence of this electric field in the second direction, and under the influence of fluid pressure in the first direction, is represented by line 136. Non-responsive cells 144 (e.g., cells that are not-responsive or substantially less responsive to the electric field) tend to move along main path 106 by fluid flow pressure into second path 110.

In one embodiment, electrode array 130 comprises a linear arrangement of electrode elements 132. In some embodiments, elements 132 of array 130 are arranged in an interleaved or interdigitated pattern. In some embodiments, electrode array 130 is exposed on a surface of body 102, while in other embodiments, electrode array 130 is disposed just below a surface body 102.

In one embodiment, electrode array 130 is configured to apply the non-uniform field as a temporally varying non-uniform field (i.e., a traveling wave non-uniform electric field) to move these cells or particles along substantially the whole distance across fluid flow path 104. In one embodiment, electrode array 130 is used to achieve this temporally varying non-uniform field by linking every fourth electrode element 132 together to form a signal channel (e.g., channel A) to permit activating and deactivating those linked elements 132 together as a single unit. By repeating this arrangement, all of the electrode elements 132 are distributed into four operational sets in which each set defines a channel to enable four distinct signal channels (e.g., channels A, B, C, D) to be applied to electrode array 130 for implementing independent driving of each of the four operational sets. In this manner, electrode array 130 enables application of a temporally varying non-uniform electric field.

In one embodiment, field-responsive cells 142 are target cells and the non-responsive cells 144 are non-target cells, while in another embodiment, field-responsive cells 142 are non-target cells and non-responsive cells 144 are target cells.

Figure 5:
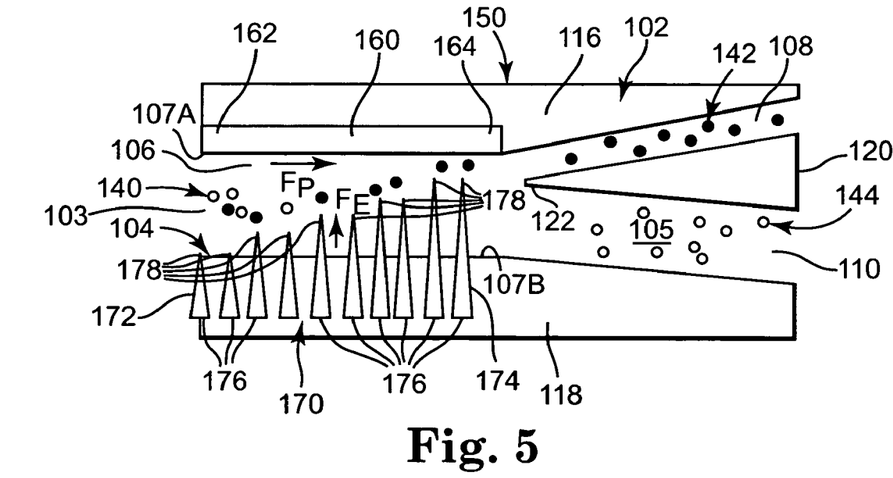
FIG. 5 is a plan view schematically illustrating a cell sorter, according to another embodiment of the present invention.

FIG. 5 illustrates sorter 150, which is one embodiment of cell sorters 20A-C (FIGS. 1-3). As shown in the embodiment of FIG. 5, sorter 150 comprises body 102 that defines a fluid flow path 104 which has substantially the same features and attributes as body 102 and fluid flow path 104 of sorter 100 (FIG. 4).

As further shown in the embodiment of FIG. 5, sorter 150 comprises first electrode structure 160 and second electrode array 170, the combination of which is an embodiment of electric field separator 44 of cell sorter 20 (FIG. 2). First electrode structure 160 is disposed on first side 107A of main path 106 and includes first end 162 and second end 164, and second electrode array 170 is disposed along second side 107B of main path 106 and includes first end 172 and second end 174. Second electrode array 172 is comprised of a plurality individual electrode elements 176 arranged generally parallel to each other, and generally perpendicular to a longitudinal axis of main path 106. Elements 176 also are generally parallel to a second direction of cell movement.

In one embodiment, each electrode element 176 comprises end portion 178. In some embodiments, end portion 178 defines a sharpened tip, which may or may not be triangularly shaped. The sharp tip of each element 176 enables application of a high field region to exert a highly focused electric field to significantly impact cells with movement in the second direction.

Moreover, in some embodiments, electrode elements 176 have different sizes. For example, as shown in the embodiment of FIG. 5, electrode elements 176 have different lengths with shorter electrode elements 176 being disposed closer to entrance 103 of fluid flow path 104 and longer electrode elements 176 being disposed closer to flow diverter 120. These longer electrode elements 176 extend further across fluid flow path 104 toward first side 107A of main path 106.

Cells 140 are moved under fluid pressure in the first direction along fluid flow path 104 (as represented by directional force arrow $F_P$). Together first electrode structure 160 and second electrode array 170 apply a non-uniform electric field as a plurality of discrete non-uniform electric fields (as represented by directional force arrow $F_E$) with each field applied between one of electrode elements 176 of array 170 and first electrode structure 160. In particular, each field extends across fluid flow path 104 between an end portion 178 of an electrode element 176 and first electrode structure 160 to cause field-responsive cells to move with a velocity component in the second direction generally transverse to the first direction.

In one embodiment, these discrete non-uniform electric fields are applied one at a time starting from electrode elements 176 at first end 172 and progressing in sequence toward second end 174 of array 170. Accordingly, the discrete non-uniform electric fields are applied at different positions along fluid flow path 104 by each of respective electrode elements 176 of array 170. In other embodiments, more than one electrode element 176 (e.g., two) are activated at a time for applying a non-uniform electric field between those multiple activated electrode elements 176 and first electrode structure 160.

This sequenced application of multiple electric fields along main path 106 effectively shuttles cells across main path 106 by small increments with each successive electrode element 176 causing each cell to move a limited distance between the end portion 178 of the element 176 (that is applying the field) and first electrode structure 160. Fluid pressure moves cells in the first direction toward diverter 120 and thereby in front of successive electrode elements 176. The application of fields by successive electrode elements 176 is synchronized with a rate of flow of cells 140 in fluid flow path 104 in the first direction so that the time of application of each field generally corresponds to the expected position of the cells as they flow down fluid flow path 106. After a series of small movements in the second direction from each successive element 176, cells 142 are moved substantially the entire distance across main path 106, or at least far enough to pass into first path 108 to achieve separation from cells 144 that are not responsive (or substantially less responsive) to these electric fields. In another embodiment of sorter 150, instead of being a single element, first electrode structure 160 is comprised of multiple electrode elements arranged together along first side 107A of main path 106 that act as a single electrode element.

Figure 6:
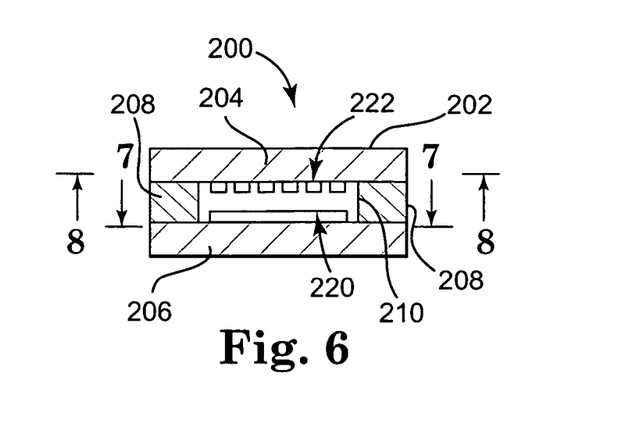
FIG. 6 is sectional view of a cell sorter, according to another embodiment of the present invention.

FIG. 6 is a partial sectional view that schematically illustrates sorter 200, which is one embodiment of cell sorters 20A-C (FIGS. 1-3). As shown in the embodiment of FIG. 6, cell sorter 200 comprises body 202 with first substrate 204, second substrate 206, and sides 208, thereby defining passageway 210 which acts as a fluid flow path. Within passageway 210, first electrode array 220 is disposed on second substrate 206 and second electrode array 222 is disposed on first substrate 204. Accordingly, in one embodiment, electrode array 220 and electrode array 222 are spaced from each other and vertically disposed relative to one another in a generally parallel arrangement with passageway 210 (e.g., fluid flow path) disposed therebetween (i.e., interposed between).

In one embodiment, electrode arrays 222 and 220 are disposed on a surface of respective substrates 204, 206 while in another embodiment, electrode arrays 222 and 220 are disposed just below a surface of the respective substrates 204, 206.

Figure 7:
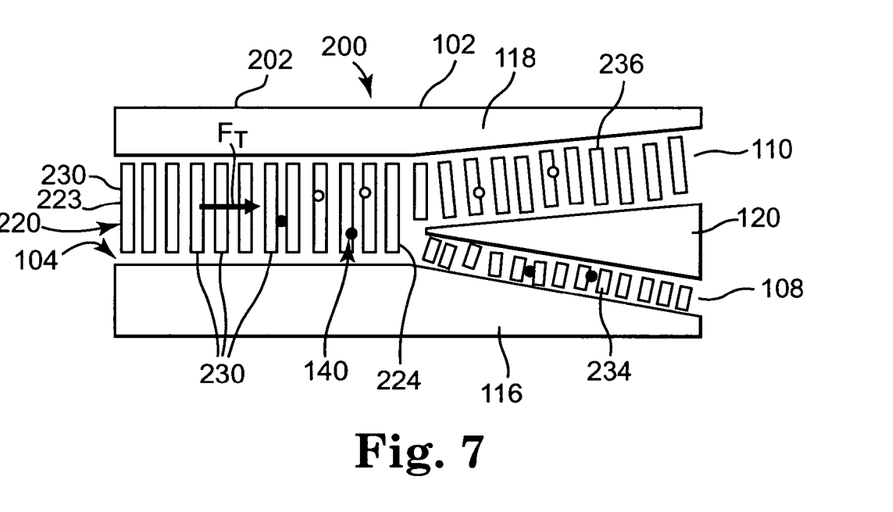
FIG. 7 is sectional view of the cell sorter of FIG. 6 as taken along lines 7-7, according to an embodiment of the present invention.

FIG. 7 is a sectional view of cell sorter 200 as taken along lines 7-7 of FIG. 6, schematically illustrating first electrode array 220. As shown in the embodiment of FIG. 7, second substrate 206 comprises body 102 and fluid flow path 104, which have substantially the same features and attributes as body 102 and fluid flow path 104 of the embodiments of FIGS. 4 and 5.

As shown in the embodiment of FIG. 7, first electrode array 220 is comprised of electrode elements 230 and arranged to extend through path 104 with a main portion extending from first end 223 to second end 224, a secondary portion 234 extending into and through first path 108, and a secondary portion 236 extending into and through second path 110. With this arrangement of electrode elements 230, electrode array 220 applies a temporally varying non-uniform electric field to move cells 140 in the first direction along fluid flow path 104 (as represented by directional force arrow $F_T$). This electric field induces motion of cells 140 within a fluid medium (e.g., a buffer solution) instead of transporting cells 140 under a fluid flow pressure (as in the embodiments of FIGS. 4 and 5).

First electrode array 220 comprises a linear arrangement of electrode elements 230. In some embodiments, elements 230 of array 220 are arranged in an interleaved or interdigitated pattern. In some embodiments, electrode array 220 is exposed on the surface of second substrate 206, while in other embodiments, electrode array 220 is disposed just below the surface of second substrate 206. Moreover, in one embodiment, first electrode array 220 has substantially the same features and attributes as electrode array 130 (the embodiment of FIG. 4) with respect to linking of every fourth element 230 of array 220 into a set of elements 230 that is independently activable, in cooperation with other sets of linked elements, in order to apply the non-uniform electric field with a temporally varying effect. Stated another way, elements 230 operate in cooperation to produce a traveling wave effect along the direction FT.

Figure 8:
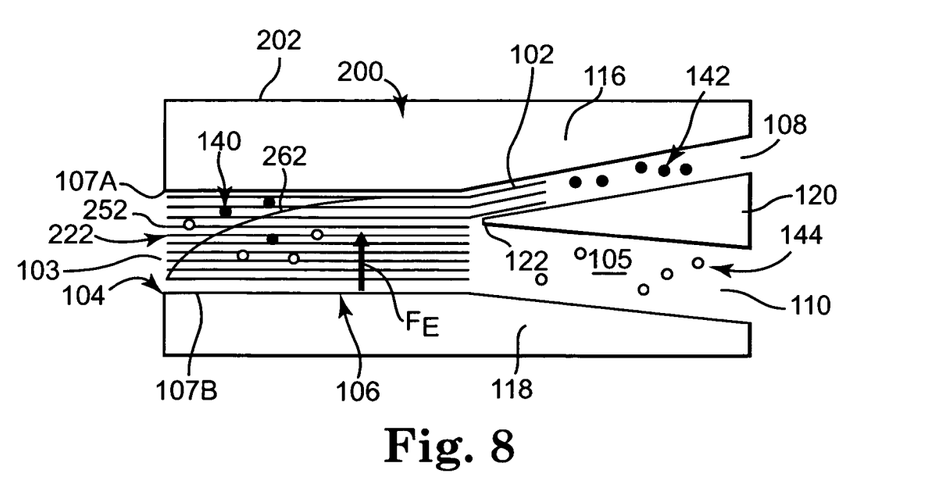
FIG. 8 is a sectional view of the cell sorter of FIG. 6 as taken along lines 8-8, according to an embodiment of the present invention.

FIG. 8 is a sectional view of FIG. 6 as taken along lines 8-8, which schematically illustrates electrode array 222, which is an embodiment of electric field separator 44 of cell sorter 20 (FIG. 2). As shown in the embodiment of FIG. 8, electrode array 222 of electrode elements 252 includes features and attributes substantially the same as electrode array 130. Electrode array 222 enables application of a traveling wave to induce field-responsive cells 142 to move with a velocity component in the second direction generally transverse to the first direction of cell transport for separating field-responsive cells into first path 108 away from non-responsive cells 144 (those that do not respond or respond substantially less to the electric field). In one embodiment, one path of field-responsive cells moving under the influence of this electric field with velocity components in the first and second directions is represented by line 262 in FIG. 8. As in other embodiments, non-responsive cells 144 are permitted to travel into second path 110.

In one embodiment, the electric fields generated by respective electrode arrays 220, 222 are applied simultaneously. In other embodiments, the electric fields generated by electrode arrays 220, 222 are applied alternately in cycles.

As illustrated by the embodiments of FIGS. 6-8, cell sorter 200 includes two electrode arrays vertically disposed relative to each other. The first electrode array 220 exerts a first temporally varying non-uniform electric field for transporting cells along fluid flow path 104, and the second electrode array 222 applies a second temporally varying non-uniform electric field to induce field-responsive cells 142 to move generally transversely in the second direction across main path 106 for separation away from non-responsive cells.

Referring again to FIGS. 6-8, in some embodiments, an applied deflection frequency for the electrode array 222 is cell-selective whereas an applied transport frequency for the electrode array 220 is not cell-selective. Electrode array 222 preferably transports all of the cells. As such, a transport frequency to be applied to array 222 is preferably selected that will exert a substantial force on all the cells along the transport direction $F_T$. On the other hand, electrode array 220 is utilized to separate different cell types. As such, the applied deflection frequency 220 is preferably selected to only apply a maximum or substantial force on the cells to be directed to output fluid path 108. Thus, in some embodiments, the two electrode arrays 220 and 222 will preferably be activated with two different operating frequencies.

Accordingly, a separation of target cells from non-target cells is enhanced through the combined use of two separate temporally varying non-uniform electric fields applied from two separate electrode arrays that are vertically disposed from each other on opposite sides of a fluid flow of cells.

Figure 9:
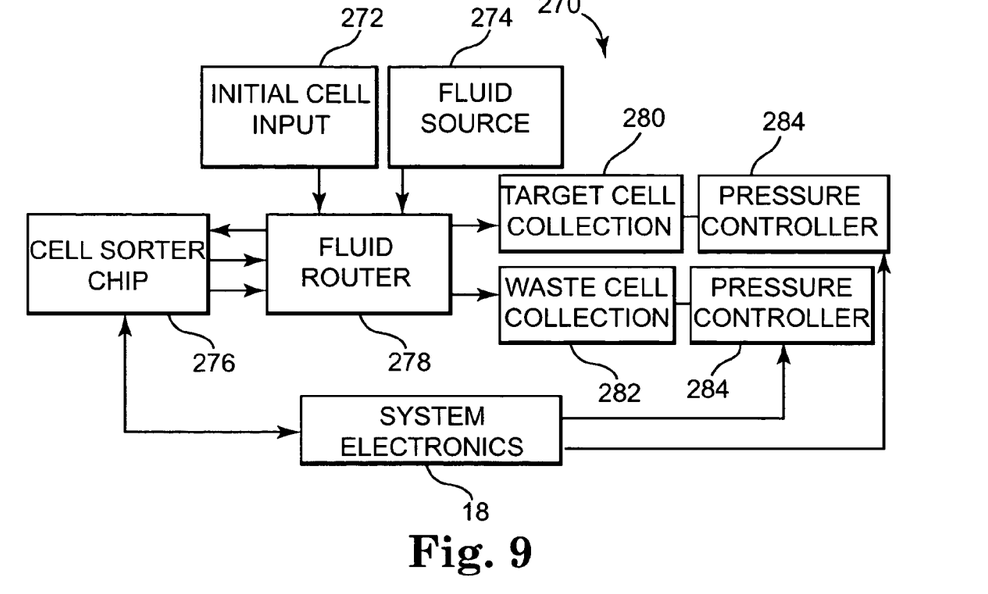
FIG. 9 is a block diagram of a cell sorter system, according to another embodiment of the present invention.

FIG. 9 is a block diagram of a cell sorter system, according to another embodiment of the present invention. As shown in the embodiment of FIG. 9, system 270 comprises initial cell input 272, fluid source 274, cell sorter chip 276, fluid router 278, target cell collection module 280, waste cell collection module 282, pressure controllers 284, and system electronics 18. In one embodiment, cell sorter chip 276 comprises an array of sorter units, such as cell sorter chip 300 described in association with FIG. 10. In other embodiments, cell sorter chip 276 comprises any one of the cell sorter embodiments of FIGS. 1-8.

In one embodiment, initial cell input 272 and fluid source 274 have substantially the same features and attributes as cell source(s) 14 and fluid source(s) 13 of the embodiment of FIG. 1. Fluid router 278 comprises a manifold or other mechanism for directing a flow of fluids (including cells) through multiple separate channels into and out of cell sorter chip 276. In addition, after cell sorter chip 276 sorts target cells from non-target cells, fluid router 278 directs target cells from cell sorter chip 276 into target cell collection module 280 and directs non-target cells from cell sorter chip 276 into waste cell collection module 282. In some embodiments, pressure controllers 284 are controlled by system electronics 18 and support fluid router 278 in maintaining a fluid pressure suitable for enabling fluid flow throughout system 270. In one embodiment, system electronics 18 has substantially the same features and attributes of system electronics 18 of the embodiment of FIGS. 1-3 for directing operation of cell sorter chip 276 and/or other components of system 270.

Figure 10:
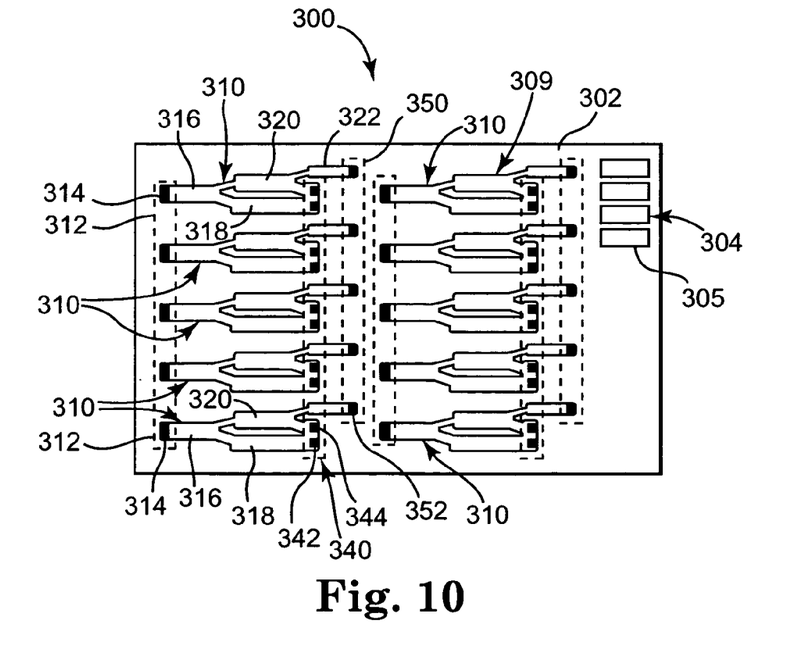
FIG. 10 is a plan view schematically illustrating a cell sorter chip, according to an embodiment of the present invention.

FIG. 10 is a plan view of one embodiment of cell sorter chip 300. In one embodiment, cell sorter chip 300 is used as part of system 270, acting as an embodiment of cell sorter chip 276. In other embodiments, cell sorter chip 300 is implemented in other cell sorter systems.

As shown in the embodiment of FIG. 10, cell sorter chip 300 comprises substrate 302, input/output array 304 of contact elements 305, array 309 of sorter units 310, input channel 312, non-target output channel 340, and target output channel 350. In one embodiment, each sorter unit 310 comprises input 314, first separator 316, second separator 320, along with non-target chamber 318, target chamber 322, first and second non-target outputs 342, 344 and target output 352.

In one embodiment, substrate 302 comprises a silicon or semiconductive structure in which various features (e.g., separators, channels, chambers, etc.) of cell sorter chip 300 are made by forming those features into a surface and/or a subsurface structure of substrate 320 using microfabrication techniques known to those skilled in the art.

Input/output array 304 enables communication with system control electronics 18 or other controller for directing operation of each sorter unit 310 as well as directing fluid flow on cell sorter chip 300. In one embodiment, sorter units 310 operate in parallel to each other, (i.e., each sorter unit 310 simultaneously sorting a volume of substantially the same population of cells) so that a significant volume of cells can be sorted in a short period of time. In another embodiment, each sorter unit 310 is operated non-simultaneously with other sorter units 310 of cell sorter chip 300.

In one embodiment, input channel 312 comprises a common input of cell(s) and fluid(s) for each sorter unit 310 via communication with input 314 of sorter unit 310. First separator 316 and second separator 320 comprise a portion of each sorter unit 310 that comprise one or more embodiments of FIGS. 1-8 for causing separation of target cells from non-target cells. Upon exerting its separating influence on a population of different types of cells, first separator 316 directs target cells into second separator 320 and directs non-target cells into non-target chamber 318, which then flow into first non-target output 342. Upon exerting its separating influence on cells from the target output of first separator 316, second separator 320 directs its non-target cells into non-target output 344 and directs its target cells into target chamber 322, which then flow into target output 352. Target output 352 from each sorter unit 310 feeds target cells into target output channel 350 while first and second non-target outputs 342, 344 feed non-target cells into non-target output channel 340.

In one embodiment, fluids and cells enter input channel 312 from a fluid router or manifold, such as fluid router 278 shown in FIG. 9, while target cells exit sorter unit 310 via target output channel 350 into a collector, such as target cell collection module 280 shown in FIG. 9. Likewise, non-target cells exit sorter unit 310 via non-target output channel 340 into a collector, such as waste cell collection module 282 shown in FIG. 9.

Embodiments of the present invention enable enhanced sorting of target cells from non-target cells by using a series of cell sorters in which the cell sorters use different sorting frequencies and/or use various forms of non-uniform electric fields to exert a separating influence on the cells within each cell sorter in the series. These embodiments enable more precise sorting of different types of cells in faster time periods.

Although specific embodiments have been illustrated and described herein, it will be appreciated by those of ordinary skill in the art that a variety of alternative and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of sorting cells comprising:
providing a fluid flow path for moving cells through a series of cell sorters in a first direction with an output of a preceding cell sorter of the series communicating with an input of a successive cell sorter of the series;
separating, within each cell sorter, a first portion of the cells away from a second portion of the cells and toward the output of a respective cell sorter by applying a first temporally varying non-uniform electric field via a first electrode array to cause movement of the first portion of the cells in a second direction across the fluid flow path, the second direction having a component generally transverse to the first direction;
wherein separating the first portion of the cells from the second portion of the cells further includes
interposing the fluid flow path in each cell sorter between the first electrode array and a second electrode array that is vertically disposed relative to the first electrode array, and applying a second temporally varying non-uniform electric field from the second electrode array to maintain transport of the first portion and the second portion of cells along the fluid flow path in the first direction during movement of the first portion of cells across the fluid flow path in the second direction.

2. The method of claim 1 wherein the first portion of the cells are target cells to be collected and the second portion of the cells are non-target cells to be discarded.

3. The method of claim 1 wherein the second portion of the cells are target cells to be collected and the first portion of the cells are non-target cells to be discarded.

4. The method of claim 1, further comprising applying the first temporally varying non-uniform electric field in at least two cell sorters of the series via:
applying a first frequency at a first cell sorter of the at least two cell sorters of the series, wherein the first frequency corresponds to a frequency at which the first portion of the cells and a third portion of the cells respond to the electric field with movement in the second direction and at which the second portion of the cells responds substantially less to the electric field with movement in the second direction; and
applying a second frequency at a second cell sorter of the at least two cell sorters of the series, wherein the second frequency corresponds to a frequency at which the first portion of the cells respond to the electric field with movement in the second direction and at which the third portion of the cells responds substantially less to the electric field with movement in the second direction.

5. The method of claim 1, further comprising applying the first temporally varying non-uniform electric field in at least two cell sorters of the series via:
applying the temporally varying non-uniform electric field at a different frequency in three or more cells sorters, wherein the different frequency in each cell sorter corresponds to a frequency at which the first portion of cells responds to the electric field with movement in the second direction and at which at least one of a plurality of portions of the cells, including the second portion of the cells, responds substantially less to the electric field with movement in the second direction.

6. The method of claim 1 wherein interposing the fluid flow path between the first electrode array and the second electrode array comprises:
arranging the first electrode array as a plurality of electrode elements generally parallel to each other in a spaced relationship with each electrode element generally parallel to a longitudinal axis of the fluid flow path; and
arranging the second electrode array as a plurality of electrode elements generally parallel to each other in a spaced relationship with each electrode element generally perpendicular to the longitudinal axis of the fluid flow path.

7. The method of claim 1 further comprising:
applying the first temporally varying non-uniform electric field alternately with applying the second temporally varying non-uniform electric field.

8. The method of claim 1 wherein the first temporally varying non-uniform electric field has a first operating frequency and the second temporally varying non-uniform electric field has a second operating frequency different than the first operating frequency.

9. A cell sorter system for a biodevice comprising:
a plurality of cell sorters arranged in series including a first cell sorter and a second sorter, wherein each respective cell sorter includes:
a fluid flow mechanism configured to maintain a fluid flow of cells in a first direction from an input to a first flow outlet and to a second flow outlet; and
an electrode array configured to apply a temporally varying non-uniform electric field to the cells to move at least one portion of the cells in a second direction having a component generally transverse to the first direction,
wherein the first flow outlet of the first cell sorter is in communication with the input of the second cell sorter,
wherein the electrode array of the first cell sorter applies the temporally varying non-uniform electric field at a first frequency to cause movement of a first portion and a third portion of the cells in the second direction away from a second portion of cells until the first portion and the third portion of cells are positioned to enter the first flow outlet of the first cell sorter while the fluid flow of the respective first and third portions of cells is maintained in the first direction for passage into the first flow outlet of the first cell sorter, and
further wherein the electrode array of the second cell sorter applies the temporally varying non-uniform electric field at a second frequency to cause movement of the first portion of the cells in the second direction away from the third portion of cells until the first portion of cells is positioned to enter the first flow outlet of the second cell sorter while the fluid flow of the first portion of the cells is maintained in the first direction for passage into the first flow outlet of the second cell sorter.

10. The cell sorter system of claim 9 wherein the second portion of the cells in each of the first and second cell sorters responds substantially less to the temporally varying non-uniform electric field than the first portion or the third portion of the cells.

11. The cell sorter system of claim 9 wherein the first portion of the cells is a target group of cells and the second portion of the cells is a non-target group of cells.

12. The cell sorter system of claim 9 further comprising:
a signal generator in communication with the electrode array of each cell sorter and configured to apply the first frequency to the electrode array of the first cell sorter and to apply the second frequency to the electrode array of the second cell sorter.

13. The cell sorter system of claim 9 further comprising:
a cell diverter disposed within the fluid flow path of each respective cell sorter and configured for separating the first and third portions of the cells into the first flow outlet and the second portion of the cells into the second flow outlet.

14. A cell sorter system for a biodevice comprising:
a plurality of cell sorters arranged in series with each cell sorter of the series including:
a fluid flow path configured for directing a flow of cells in a first direction;
an electrode arrangement including a first electrode array and a second electrode array with the first electrode array configured to apply a first temporally varying non-uniform electric field for causing movement of a field-responsive portion of the cells in a second direction having a component generally transverse to the first direction and the second electrode array configured to apply a second temporally varying non-uniform electric field for causing transport of the cells along the fluid flow path in the first direction, wherein the first electrode array and the second electrode array are vertically disposed relative to one another on opposite sides of the fluid flow path with the fluid flow path interposed between the respective first and second electrode arrays; and
a cell diverter disposed within the fluid flow pathway to encourage separation of the field-responsive portion of the cells from a non-responsive portion of the cells.

15. A cell sorter system for a biodevice comprising:
a plurality of cell sorters arranged in series with each cell sorter including:
  a fluid flow pathway including a first end and a second end, and configured for directing a flow of cells in a first direction from the first end to the second end, the cells including a first portion and a second portion;
  an electrode arrangement configured for causing movement of the first portion of the cells in a second direction generally transverse to the first direction and away from the second portion of the cells by successive discrete movements of the first portion of the cells in the second direction, wherein the electrode arrangement includes:
    a first electrode structure including an array of generally parallel, spaced apart electrode elements arranged in series along a first side of the fluid flow pathway, wherein a longitudinal axis of each electrode element extends across the fluid flow pathway perpendicular to the first direction, and further wherein a length of the respective electrode elements increases successively from the first end to the second end of the fluid flow pathway; and
    a second electrode structure disposed on a second side of the fluid flow pathway and spaced from the first electrode structure,
    wherein the fluid flow pathway is interposed between the first electrode structure and the second electrode structure, and wherein the electrode structures are configured to apply a plurality of separate non-uniform electric fields successively one at a time from the first end to the second end of the fluid flow pathway with each separate non-uniform electric field being applied across the fluid flow pathway from each one of the respective electrode elements of the first electrode structure to a corresponding one of the respective electrode elements of the second electrode structure; and
  a cell diverter disposed within, and adjacent to the second end of, the fluid flow pathway to encourage further separation of the first portion of the cells, that have been moved in the second direction, away from thee second portion of the cells.

16. The cell sorter system of claim 15 wherein
the array of electrode elements of the first electrode structure arranged with selective electrode elements connected together to define independently drivable sets of electrode elements.

17. The cell sorter system of claim 15 wherein each electrode element has a generally sharpened end from which each of the respective electric fields is applied.

18. A cell sorter system for a biodevice comprising:
a plurality of cell sorters arranged in series with at least one cell sorter of the series including:
  a fluid flow path configured for directing a flow of cells in a first direction;
  an electrode arrangement including a first electrode array and a second electrode array with the first electrode array configured to apply a first temporally varying non-uniform electric field for causing movement of a field-responsive portion of the cells in a second direction having a component generally transverse to the first direction and the second electrode array configured to apply a second temporally varying non-uniform electric field for causing transport of the cells along the fluid flow path in the first direction, wherein the second electrode array extends from a main portion of the fluid flow path into and through a first port of the fluid flow path, and into and through a second port of the fluid flow path; and
  a cell diverter disposed within the fluid flow pathway to encourage separation of the field-responsive portion of the cells from a non-responsive portion of the cells.

19. A cell sorter system for a biodevice comprising:
a plurality of cell sorters arranged in series with each cell sorter including:
  a fluid flow pathway configured for directing a flow of cells in a first direction;
  an electrode arrangement configured for causing movement of a first portion of the cells in a second direction generally transverse to the first direction by successive discrete movements of the first portion of the cells in the second direction, the electrode arrangement including:
    a first electrode structure including an array of spaced electrode elements arranged in series along a first side of the fluid flow path; and
    a second electrode structure disposed on a second side of the fluid flow path and spaced from the first electrode structure,
    wherein the first and second electrode structures are configured to apply a plurality of non-uniform electric fields with each non-uniform electric field applied between a separate electrode element of the first electrode structure and the second electrode structure,
    further wherein each respective electrode element has a generally sharpened end from which the electric field is applied; and
  a cell diverter disposed within the fluid flow pathway to encourage separation of the first portion of the cells from a second portion of the cells.

* * * * *

UNITED STATES PATENT AND TRADEMARK OFFICE
CERTIFICATE OF CORRECTION

PATENT NO.       : 7,390,387 B2
APPLICATION NO.  : 10/808803
DATED            : June 24, 2008
INVENTOR(S)      : Winthrop D. Childers et al.

It is certified that error appears in the above-identified patent and that said Letters Patent is hereby corrected as shown below:

In column 10, line 24, delete "FT" and insert -- $F_T$ --, therefor.

In column 12, line 55, in Claim 1, delete "direction;" and insert -- direction, --, therefor.

In column 13, line 29, in Claim 5, delete "cells" and insert -- cell --, therefor.

In column 15, line 44, in Claim 15, delete "thee" and insert -- the --, therefor.

In column 15, line 47, in Claim 16, insert -- is -- before "arranged".

Signed and Sealed this

Twenty-eighth Day of October, 2008

JON W. DUDAS
*Director of the United States Patent and Trademark Office*